United States Patent

Renz et al.

[11] Patent Number: 6,006,608
[45] Date of Patent: Dec. 28, 1999

[54] METHOD AND APPARATUS FOR EXAMINING THE MECHANICAL-DYNAMICAL PROPERTIES OF A WORKPIECE

[76] Inventors: Rainer Renz, Cusanusstr. 39, 67663 Kaiserlautern; Olaf Reese, Am Hohenrech 15, 67705 Trippstadt, both of Germany

[21] Appl. No.: 09/031,817

[22] Filed: Feb. 27, 1998

[30] Foreign Application Priority Data

Feb. 27, 1997 [DE] Germany .......................... 197 07 968

[51] Int. Cl.⁶ .................................................. G01B 16/00
[52] U.S. Cl. .............................................. 73/800; 73/808
[58] Field of Search .......................... 73/800, 801, 808, 73/815

[56] References Cited

U.S. PATENT DOCUMENTS

| | | | |
|---|---|---|---|
| 4,015,465 | 4/1977 | Scott | 73/800 |
| 4,378,701 | 4/1983 | Mountain et al. | 73/808 |
| 4,480,480 | 11/1984 | Scott et al. | 73/769 |
| 4,719,347 | 1/1988 | Kugler et al. | |
| 4,812,052 | 3/1989 | Adam et al. | |
| 4,953,973 | 9/1990 | Laftheris et al. | 356/32 |

FOREIGN PATENT DOCUMENTS

| | | |
|---|---|---|
| 0194354 | 9/1986 | European Pat. Off. . |
| 2931332 | 2/1981 | Germany . |
| 3631153 | 3/1988 | Germany . |
| 3709598 | 10/1988 | Germany . |
| 4200173 | 7/1993 | Germany . |

OTHER PUBLICATIONS

Bauch: Workpiece Examination, H. Blumenauer (Hrsg.), 3rd Edition, Leipzig (1984), pp. 59 to 78.

Materialprufung, 36 1994 7–8 pp. 289–292, E. Becker, Software for fatigue and crack mechanical measurments.

VDI Berichte Nr. 631 1987, pp. 275–285, H–Ch. Goetting u.a., Strain measurements of multilayer components by the diffraction principle.

Materialprufung, 34 1992 1–2, pp. 23–26, P. Heuler u.a., Oscillation strength test of materials at elevated temperatures.

AVK–Meeting, Mainz, 1987, Meeting Report, pp. 38–1 to 38–9, Altstadt, V., Ehrenstein, G.W. Renz, R., Influence of Fillers on the mechnical properties of SMC materials.

*Primary Examiner*—Max Noori
*Attorney, Agent, or Firm*—Fish & Richardson P.C.

[57] ABSTRACT

Described is a procedure for investigating the mechanical-dynamic properties of a work piece, whereby the work piece is subjected to cyclical tensile and/or compression stress in a first direction. A power signal representing the tensile and/or compression stress of a work piece is produced with the use of a power-registering device and produces a length change representing at least one specified section of the work piece my means of a distance-registering device. The power signal and distance signal are fed to an evaluation device, which determines a characteristic value for the mechanical-dynamic properties of the specified section from the power signal and distance signal obtained during one stress cycle. The procedure is distinguished by the fact that the work piece provided with a raster made of contrasting coding strips along a second direction is continuously swept by a laser beam with a specified scanning frequency along the second direction, and the intensity of the laser light modulated by the coding strips is registered. The time path of the distance signal corresponds to the registered intensity of the modulated laser light, and the evaluation device determines, from the time path of the distance signal, the length changes of different sections of the work piece defined by two or more coding strips and swept by the laser light and the characteristic values of these different sections for the mechanical-dynamic properties.

17 Claims, 13 Drawing Sheets

METHOD AND APPARATUS FOR EXAMINING THE MECHANICAL-DYNAMICAL PROPERTIES OF A WORKPIECE

TECHNICAL FIELD

The invention concerns a procedure for investigating the mechanical-dynamic properties of a work piece. Moreover, the invention concerns a device for investigating the mechanical-dynamic properties of a work piece.

BACKGROUND AND SUMMARY

In many areas of material and construction technology a study of the properties of work pieces under stress is of great importance because such studies make statements about the properties of the serviceability and fatigue of the work piece possible. Such stress studies are not only performed on work pieces that consist of homogenous material, but also on work pieces of heterogenous materials such as fiber-reinforced plastics, etc.; in addition, the stress properties of connections (glued and screwed connections, weld joints) can be examined in multi-component work pieces.

It is already known to perform so-called stress-strain tests when investigating properties of work pieces under stress. In a stress-strain test the work piece is acted upon with increasing tensile stress and the resulting extension of the work piece measured. The extension can be measured, for example, by a wire strain gauge stuck onto the work piece or by a clip-on extensometer that has been clamped onto it—designated also as a "set extension sensor" Stress-strain tests can be carried out without damaging the object or until breakage occurs. They make possible a quasi-static characterization of the properties of the work piece under tension, but do not provide any information about the fatigue strength of the work piece.

To examine the fatigue strength of a work piece it is already known to perform a so-called hysteresis measurement by applying cyclical dynamic stress to the work piece in the tensile or compression area in accordance with the specifications of claim 1 and determining the mechanical-dynamic properties of the work piece and their change during the dynamic stress (see FIG. 1). Through such hysteresis measurements statements concerning damping, stiffness, and non-elastic deformation properties, in particular with polymer materials, can be made, as well as statements concerning the plastic extension properties of the work piece that cannot be obtained by clear stress-strain tests. In this regard it is of special practical significance that practical evaluative criteria concerning the fatigue properties of the work piece under real conditions of use can be collected from such mechanical-dynamic measurable characteristics of the work piece and that statements about the onset and the course of the damaging phenomena in the work piece, such as, for instance, micro-cracks, can be gathered.

As with clear stress-strain tests, hysteresis measurements can also be carried out until the work piece breaks.

In summary, it can be said in general that dynamically stressed piece parts can be considerably better characterized and more safely designed by using hysteresis measurements.

In the case of known hysteresis measurements a wire strain gauge or a clip-on extensometer is used to measure the strain.

Use of the wire strain gauge has proven disadvantageous in that it has only a relatively limited measurement area and thus is not suitable for all investigations.

Clip-on extensometers have a considerably larger measurement area (about 100% relative extension and better). Because the two measurement points between which a length change (extension) of the work piece is measures are made by cutting edges that are clamped onto the testing objects in the case of a clip-on extensometer, the danger that the cutting edge will slip arises especially with hysteresis measurements—a situation that can lead to a falsification of the measurement results with respect to the values of the interval. The effects of friction between the cutting edges and work piece can also lead to false statements, e.g., in the case of polymer materials with respect to mechanical damping. Moreover, it is unfavorable that damage to the surface of the work piece can occur through the mechanical contact between cutting edge and work piece and for this reason effects on the fatigue strength cannot be ruled out.

A fundamental disadvantage of determining the extension both by using wire strain gauges and clip-on extensometers consists in the fact that these sensors always make possible an integral measure of the extension between two fixed measurement points. In other words, the extension property is not determined outside of the measurement points, and the extension between the measurement points can only be determined with the set, specified definition given by the distance between the measurement points. Because in general only a clip-on extensometer is clamped onto the work piece due to space considerations, measurements at multiple sites are usually not possible. Different workpiece extension properties that are a function of the place therefore cannot be determined for this reason or are only capable of determination on a very limited basis.

From EP 0194354, the use of a laser measuring procedure with clear tensile tests on a sample to measure relative length changes of a sample without contact to the object is already known; in this laser measuring procedure a laser beam continuously scans the sample in the direction of draw and is reflected on a raster attached to the sample, and the reflected laser beam, whose intensity is modulated by the raster, is registered by a photodetector, through which the change in the sample's extension can be inferred by measuring the modulation frequency of the reflected laser beam.

The task of the invention is to develop the hysteresis procedure described in the introduction in a way that considerably extends the possibilities of characterizing a work piece subjected to dynamic stress known up to now, which makes possible statements about the workpiece fatigue strength and the fatigue properties, as well as possible damage processes—which can be of considerable importance to designing and dimensioning the work piece and which could not be obtained in a comparable form until now. It is, moreover, a further task of the invention to create a device through which the continuing characterization possibilities of the work piece mentioned are realized and can be distributed in suitable form.

The claimed subject matter is intended to solve these tasks.

Different sections of the work piece can be examined at the same time with respect to their mechanical-dynamic properties through the procedure according to the invention, as a result of which, for example, the determination of a local material nonhomogeneity of the work piece due to anomalous damping, stiffness, or deformation properties are made possible in one of the observed sections. In this way a weak spot that can occur in the work piece with dynamic stress can be localized and characterized in connection with different dynamic stresses. In addition, the existence of nonhomogeneities and their local spreading can be followed by monitoring the local dynamic stress properties of the work piece over time with the assistance of characteristic values measured for the different sections. In this way the fatigue properties of the work piece with respect to time and place can be characterized specific to stress. For example, a multi-component work piece that is connected by a weld seam can be examined locally in the seam area for solidification or loss of cohesion (especially with metals) under external dynamic stress. Such statements are of great interest when one is interested in testing different work pieces to determine their capability for a given use or when one is faced with the task of improving a given work piece in a way that does justice to the given demands with respect to its stability properties.

A further advantage of the procedure according to the invention consists in the fact that the workpiece sections that are to be investigated are variable—i.e., before each measurement both their position and length can be freely defined. As a result, the simple adjustment of the procedure according to the invention to different measuring demands (e.g., the demanded spatial definition of the measurement) and a reduction of the obtained test data are made possible.

Due to its property as a local investigative procedure, the procedure according to the invention is especially well suited for the investigation of multi-component work pieces or heterogenous work pieces with locally differing structures.

Instead of laser beams, a collimated light beam from a non-laser scanning source can be used for scanning the raster.

When the direction of the cyclical tensile and/or compression stress (first direction) coincides with the direction of the raster and the laser scanning (second direction), the measurement of the characteristic value(s) occurs directly in the direction in which the power is introduced. The direction of the longitudinal extension of the raster—i.e., the direction vertical to the coding strips that make up the raster—is designated by the direction of the raster.

Because the laser beam has a finite scanning speed, the values for the length changes of the monitored sections are recorded at different points in time by a laser scan. To rule out this undesired effect and increase measuring precision it is preferred to assign a particular absolute reference time ($t_i$) to the distance signal of each laser scan within the framework of the evaluation and to calculate the length changes of the different sections with respect to the assigned fixed reference time ($t_i$) for each laser scan.

In accordance with an appropriate variation of the model of the present invention, for each workpiece section the distance signal (which, if applicable, is previously formed by impulses) is transformed into a digital signal of the section length change that represents the length change of the corresponding section between two successive laser scans. These digital signals of the section length changes assigned to the respective sections can then be fed to a sequential computer, which determines one or several of the characteristic values of each workpiece section by means of a stored computer program while taking into consideration the digitized power signal from an A/D converter.

In this case the correction of the signal of the section length change obtained during a single laser scan that was already mentioned can be carried out by a calculation of the computer program. It calculates the corresponding corrected values valid for the fixed reference time $t_i$ from the values of the signals of the section length change obtained during the scan by means of an interpolation procedure. The characteristic values are then determined on the basis of these corrected values.

A comparison of the characteristic values determined for different sections of the work piece—for example through difference formation—makes possible considering the changes of the characteristic variables along the path of the raster on the work piece.

Moreover, the properties of the curves of the damping distribution and/or the tensile and compression stiffness and/or the non-elastic deformation and/or the plastic extension over time can be followed by using a graphics program in real time stored in the sequential computer; and those curves can be represented graphically, for example, by transforming the work piece into a false color representation.

Although in principle cyclical stress can be carried out alone in the tensile or compression area, the preferred method is to exert cyclical stress by alternating between the tensile and compression areas because in this way different properties in the tensile and compression areas can be determined and characterized in a single experiment.

The dynamic path of an oscillation cycle can be varied in a wide range, and it has been proven that especially sine-shaped and triangular or rectangular dynamic paths create favorable conditions for the mechanical-dynamic investigation of a work piece.

According to an especially preferred working model of the procedure, the work piece is exposed to a time sequence of different stress levels, which are superimposed by cyclical tensile and/or compression stress (i.e., tensile or compressional vibration). Through such so-called stress-increase tests information can be obtained about the stress-dependent properties (for example, with respect to the transition from the linear visco-elastic area at the low stress levels that occur with polymers to the nonlinear visco-elastic area at higher stress levels; and statements can be made about the onset of irreversible damage to the work piece. In addition, by the cyclical repetition of the stress-increase test, clues can be obtained about the speed of deterioration and by comparing the characteristic values obtained at each repetition of the sequence of the stress level with respect to the same stress level each time, it is possible, in the meantime, to follow the effect of low or high stress on irreversible damage.

According to an especially preferred variation of the stress-increase test, the stress can be brought back down to a basic stress level with a low stress value after each stress level and the comparison of the characteristic value(s) mentioned can be carried out at this basic stress level. In this way possible damage caused in the meantime by higher stress can be exactly recognized and analyzed.

According to another advantageous variation of the model of the invention the procedure can be used, moreover, to determine the transversal contraction of the work piece by having a stationary pencil of light, emitted from a light source, partially shaded by a cross dimension that is larger than the cross dimension of the work piece, whereby the intensity of the remaining light that is not shaded by the work piece is captured by a detector and transformed into a signal characterizing the cross dimension of the work piece. This, for example, makes possible determining the transversal contraction of the work piece by varying the tensile stress.

If the extension of the light spot produced from the pencil of light on the work piece in the second direction (i.e., the direction of the raster) essentially corresponds to the length of one or several of the workpiece sections under consideration, determining the transversal contraction of the work piece in the area of one or several of the sections under consideration becomes possible.

A refinement of the cross dimension measurement of the work piece can be obtained when the work piece is equipped with another raster made of contrasting coding strips in a third direction and another laser is used whose laser beam sweeps the additional raster; thus the extension properties of the work piece are determined locally in the third direction in a way similar to the way the extension in the first direction is measured. In this way the contraction or extension properties of the work piece can be obtained at the same time; and they can be obtained locally in the second and third direction (i.e., for instance, in the longitudinal and transverse direction to the direction from which the power is introduced) and put into relationship with each other—which can then be of interest if the cracks that form in fiber-reinforced material with longitudinally running fibers are to be analyzed.

Both the integral (if applicable, limited to a section) measurement of the cross dimension and the local measurement of the distribution of the cross dimension of the work piece by using the additional raster make determining Poisson's ratio—the ratio of the longitudinal extension to the transversal contraction—possible in a single experiment. In the case in which the distribution of the cross dimension is measured, the additional raster on the work piece can be attached to a side across from the first raster.

Through a possible local and/or temporary warming or cooling of the work piece the procedure according to the invention can be extended advantageously to the analysis of temperature-dependent phenomena. For the analysis of the mechanical-dynamic properties of the work piece under consideration warming without contact to the object is appropriate.

The problem that the present invention seeks to clear up is solved by the device according to claim 13.

Accordingly, the maximum spatial definition is determined by using the device to measure through the center distance of two successive coding strips, whereby one must, however, take into consideration the fact that with a reduction of the center distance, the thickness of the coding strip must necessarily be reduced, as a result of which the modulation intensity of the modulated laser beam decreases. This has the consequence that in practice a lower limit is specified for the center distance of two successive coding strips. It has been shown that favorable measuring conditions exist when the center distance lies in the range between 0.5 and 10 mm, and especially between 2 and 5 mm.

Within the framework of the stress-increase tests already mentioned, the data-processing device preferably has a computer program that compares the characteristic values obtained for the same stress levels with each repetition of the sequence of stress levels.

Further advantageous refinements of the procedure according to the invention and the device according to the invention can be inferred from the subclaims. The invention is described by using examples with the help of the drawings below. The following figures are used.

DETAILED DESCRIPTION

Figure 1:
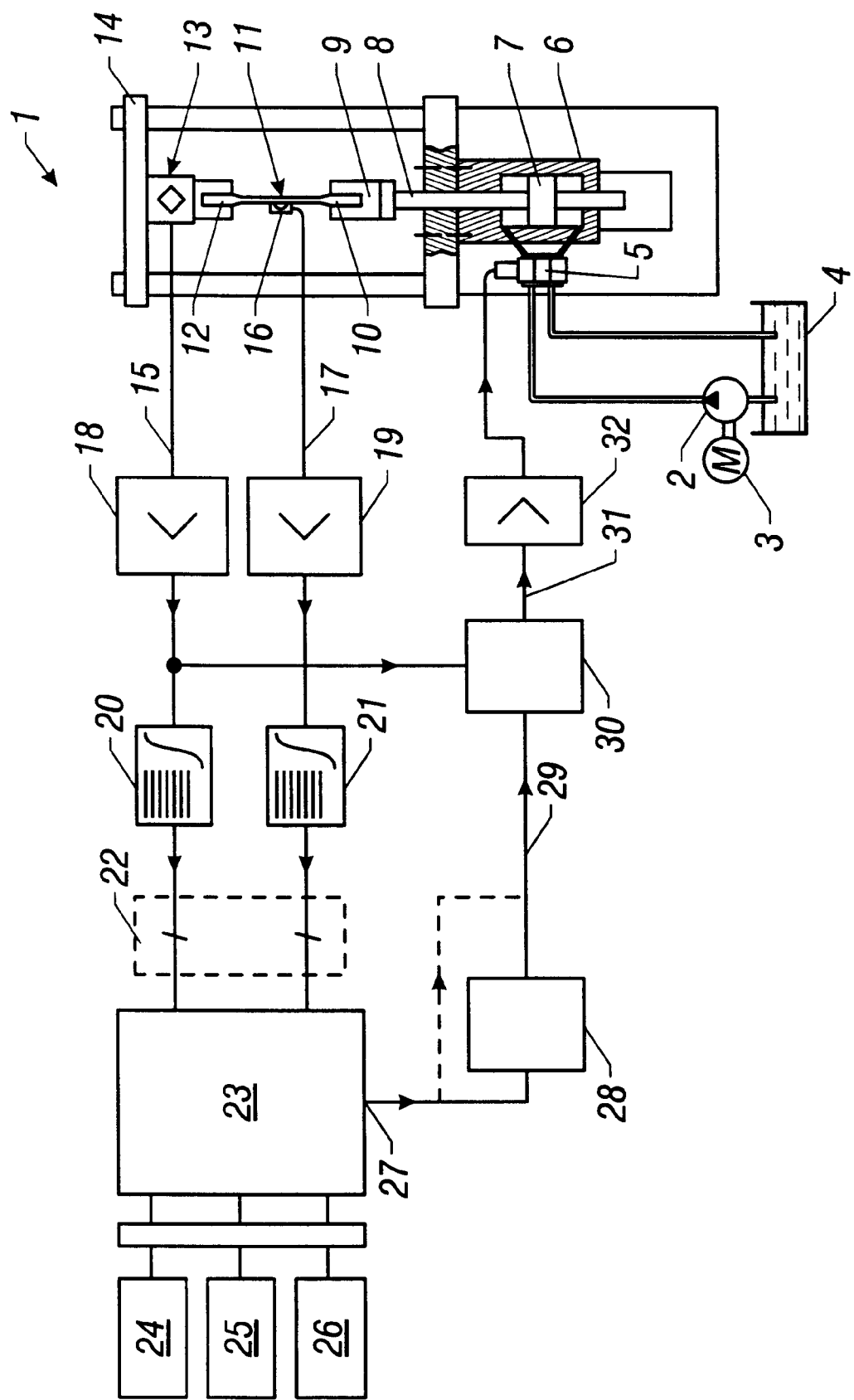
FIG. 1 is a diagrammatic representation of a hysteresis measuring device according to the prior art.

According to FIG. 1, a known hysteresis measuring device includes a servo-hydraulic testing machine 1 with an electric motor 3 that is driven by a hydraulic pump 2 that presses hydraulic oil from a reservoir 4 to an electrically controlled pilot valve 5 and from there into a piston-cylinder system 6 consisting of two chambers. The piston 7 is connected firmly to a piston rod 8, whose free end 9 holds one end 10 of the work piece 11 being analyzed. The other end 12 of the work piece is connected to the mouth of a load cell 13. The load cell 13 is anchored firmly to the frame 14 of the servohydraulic testing machine 1.

As one can also see from FIG. 1, a clip-on extensometer 16, which obtains the length change of a set, specified section of a work piece 11 by means of a two-point measure and emits a corresponding path signal 17, is clamped to the work piece 11 with the known hysteresis measuring procedure.

Within the framework of the further processing of the signal, the power signal 15 and the path signal 17 are fed to an amplifier 18 or 19, then digitized by A/D converters 20, 21, and then—if applicable—fed to a computer 23 after intermediate storage in a digital memory 22. Peripheral equipment (mass memory 24, printer 25, plotter 26) is connected to the computer 23.

A control outlet 27 of the computer 23 is connected to the mouth of a function generator 28, which supplies a set-point signal 29 for a controller 30. After comparing the set-point signal 29 with that of the power signal, which is amplified and covered by the load cell 13, the controller 30 produces as an instantaneous value a control signal 31, which is amplified in an amplifier 32 and then fed to the control input of the pilot valve 5.

The known device's operation according to FIG. 1 is explained below.

The computer 23 takes on the tasks of process control through the control outlet 27 by specifying the tensile and compression movement of the piston 7 in a power-controlled manner with the help of the function generator 28 and the control loop essentially formed by the controller 30, the pilot valve 5, and the load cell 13. In addition, the computer 23 serves to obtain and evaluate the test values by feeding the digitized power and path signals 15, 17 to it and evaluating them according to the computer program stored in a computer 23 within a framework of a numeric hysteresis evaluation. The known hysteresis evaluation is represented below in FIGS. 2a and 2b for polymers and in FIG. 2c for metals.

Figure 2A:
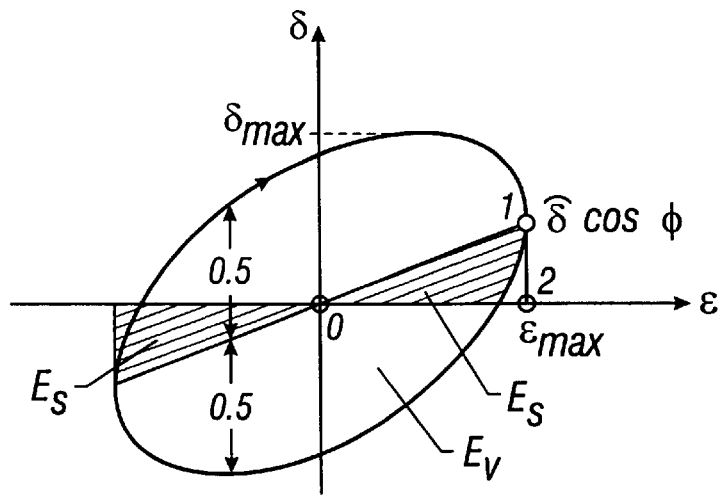
FIGS. 2a, 2b, and 2c show diagrams explaining the evaluation of hysteresis loops according to the prior art.

To illustrate the principle of hysteresis evaluation, we first start, in FIG. 2a, with a linear visco-elastic property of the material, which in practice occurs with polymers having only small oscillation deflections. Assuming a sine-shaped stress σ(t), an extension ε(t) occurs that is not in phase with the stress due to internal damping:

$$\epsilon(t) = \epsilon_{max} \sin \omega t;\ \sigma(t) = \sigma_{max}(\omega t + \phi) \quad (1)$$

(ω: radian frequency; φ: phase shift).

The hysteresis evaluations are based on the fact that the phase shift φ and the storage $E_s$ and loss $E_v$ are obtained by a suitable geometrical analysis of the ellipse. As represented in FIG. 2a, storage $E_s$ is the content of the shaded triangular surface 012 under the center line 01 and the point-symmetric shaded triangular area across from it:

$$E_s = \sigma_{max}\ \epsilon_{max} \cos \phi. \quad (2)$$

The loss is the area of the entire hysteresis loop:

$$E_v = \pi \sigma_{max}\ \epsilon_{max} \sin \phi. \quad (3)$$

The quotient of the loss and storage is designated as damping variable Λ and corresponds, in essence, to the phase shift:

$$\Lambda = E_v/E_s = \pi \tan \phi. \quad (4)$$

Figure 2B:
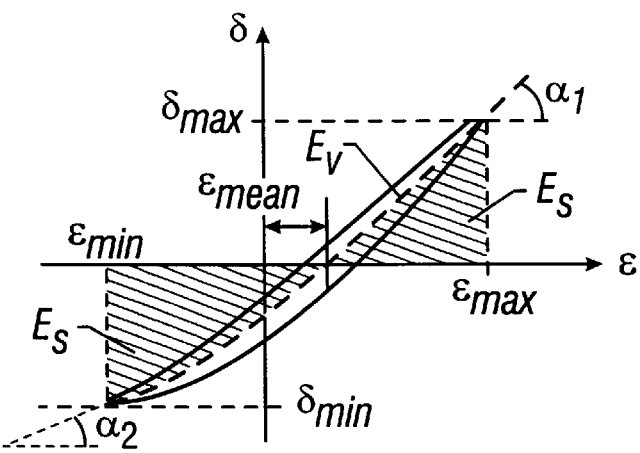

FIG. 2b shows a hysteresis curve in the area of nonlinear visco-elastic properties of material as typically arises with polymers at higher dynamic stresses. With nonlinear visco-elastic properties a definition of the phase angle φ no longer exists. In this case equations (1) to (4) are no longer valid. The hysteresis curve, nevertheless, provides significant information about the nonlinear deformation properties of the work piece.

The internal damping $\Lambda = E_v/E_s$ now takes on the meaning of a dimensionless characteristic magnitude for describing the energy-dissipating processes of an oscillation. It is a measure of the material strain and breakdown.

The material stiffness can be obtained as an increase of the center curve $\tan \alpha_1$ and $\tan \alpha_2$ at the reversal points of the center curve $\epsilon_{max}$ and $\epsilon_{min}$. The change in stiffness with successive oscillations is a measure for the damage that occurs during fatigue stress. For example, the formation of cracks leads to a clear decrease in stiffness in the tensile phase.

The intersection point of the center curve and the extension axis at the mean stress determines the mean extension $\epsilon_{mean}$. The mean extension $\epsilon_{mean}$ is another important characteristic magnitude because it describes the cyclical creeping of a material due to plastic deformation such as the formation of cracks or delamination.

Figure 2C:
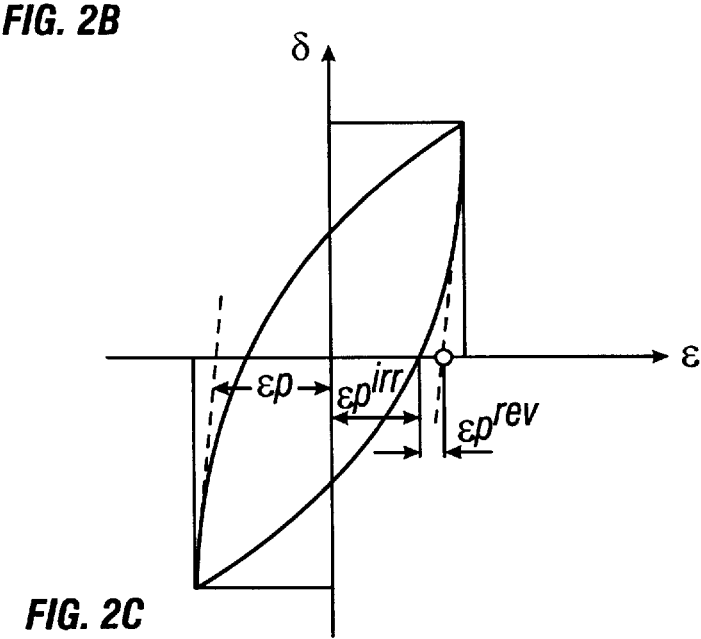

FIG. 2c shows a hysteresis loop as is typically obtained with metal materials. An important characteristic magnitude for evaluating solidification or loss of cohesion processes that occur in metals is the plastic extension $\epsilon_p$ or its time path under dynamic stress. The plastic extension $\epsilon_p$ consists of an irreversible share $\epsilon_p^{irr}$ and a reversible share $\epsilon_p^{rev}$ and can be obtained from the hysteresis loop, as is shown in the diagram in FIG. 2c.

The determination of the characteristic values mentioned then takes place in the computer 23 with the use of a numerical analysis of the hysteresis loop obtained from the power and path signals by means of a specified computer program, as is shown in FIGS. 2b and 2c.

Figure 3:
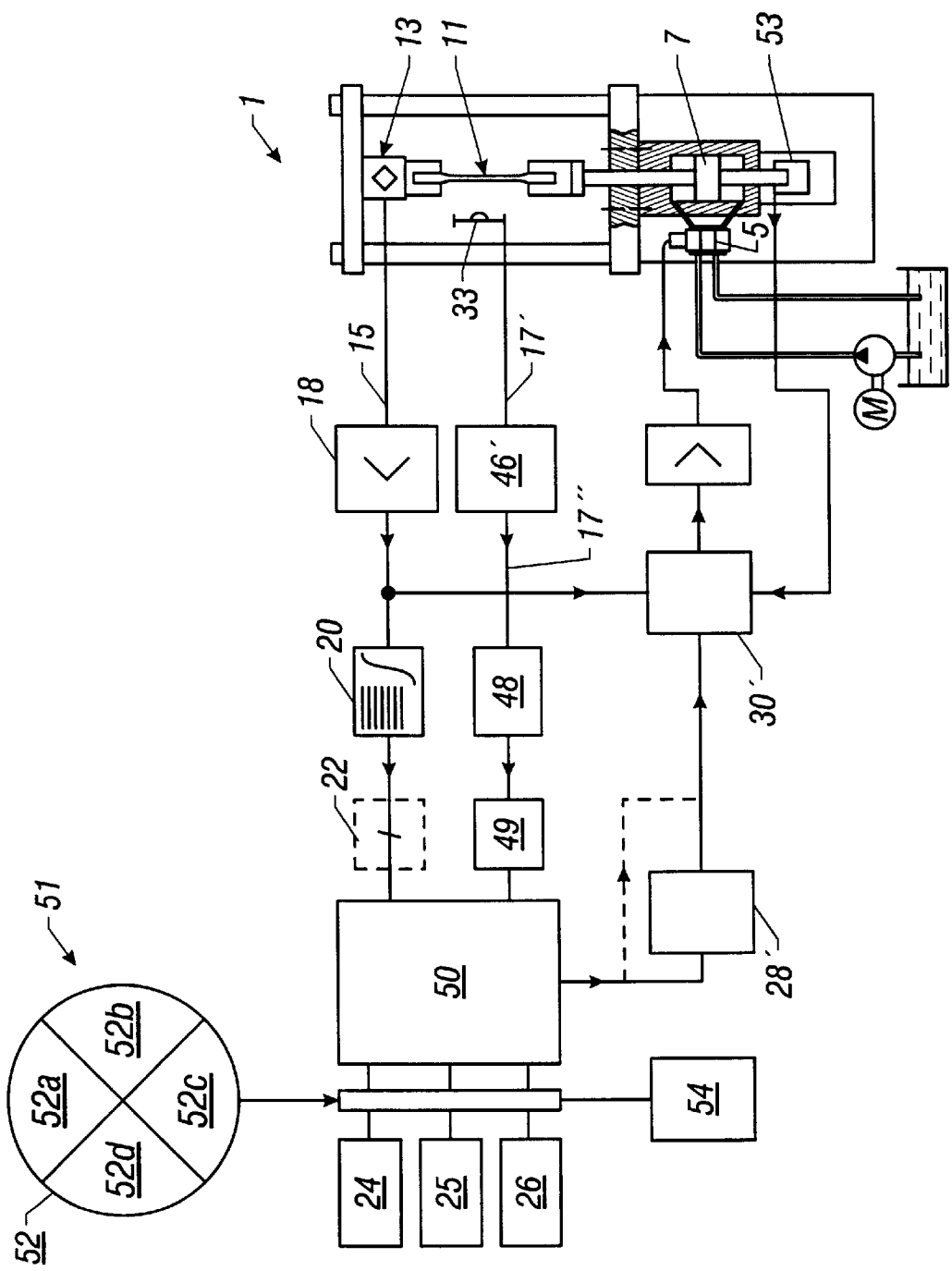
FIG. 3 shows a diagrammatic representation illustrating the function of a hysteresis measuring desk designed according to the invention.

FIG. 3 serves to illustrate a variation of the procedure according to the invention and shows an example of a test stand that is designed to carry out the procedure according to the invention. In this connection, the same parts that are in FIG. 1 are designated with the same reference number, and the corresponding description of the parts in FIG. 1 are referred to.

The device according to FIG. 3 shows a laser extensometer 33 (explained in greater detail later in connection with FIGS. 4 and 5) for registering the distance instead of the clip-on extensometer 16 from FIG. 1.

Figure 4:
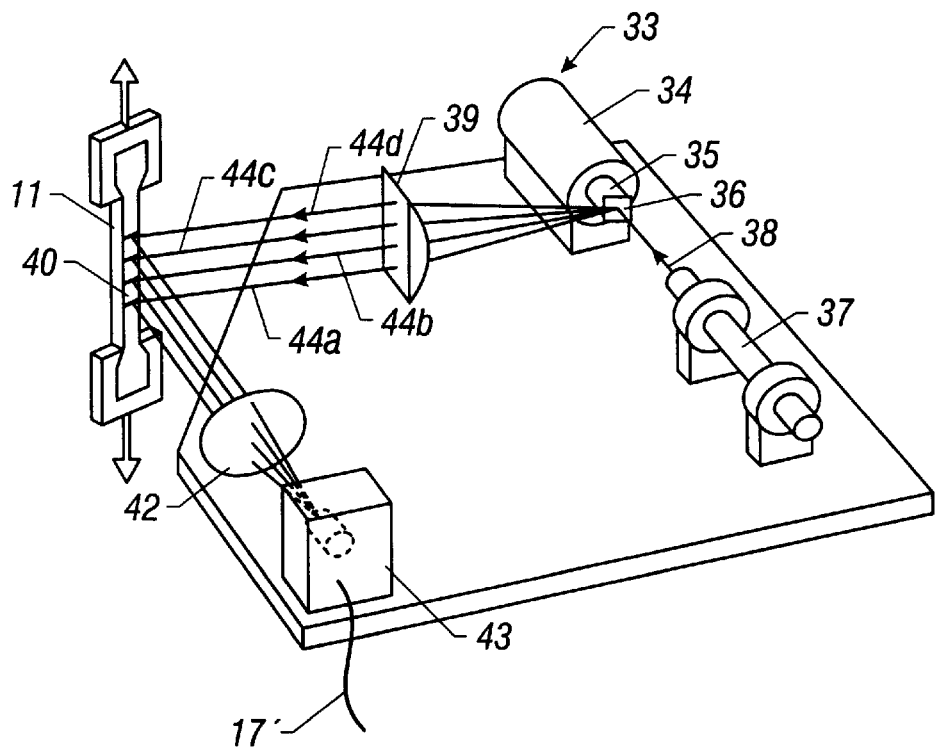
FIG. 4 shows a diagrammatic view of a laser extensometer used in the procedure according to the invention.
Figure 5:
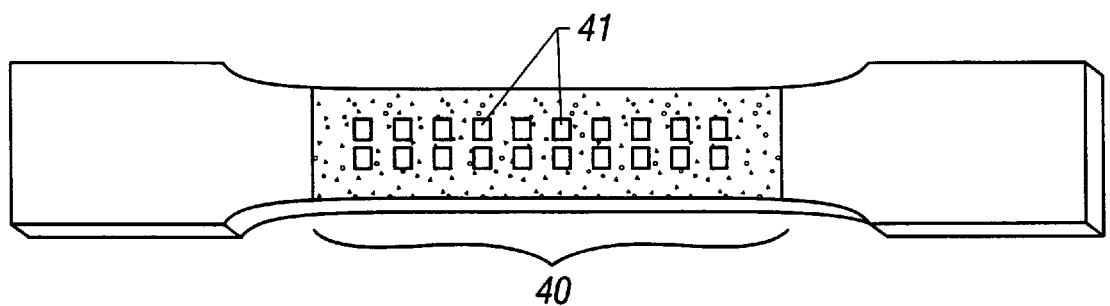
FIG. 5 shows a representation of a raster made of coding strips.

According to FIG. 4 a motor 34 drives a rotating mirror 36 attached to the front of the motor shaft 35, which can be constructed, for example, as a planar deviation mirror with a mirror surface placed at a 45° angle to the rotational axis. A laser beam 38 produced from a laser 37 falls in axial direction on the rotating mirror 36 and is cast from it at a 90° angle to a cylinder lens, which is placed at a distance corresponding to its focal range from the center of the rotating mirror 36. The work piece 11, whose surface is provided with a raster 40 made of reflecting coding strips 41 (shown in greater detail in FIG. 5), is located in the beam path behind the cylinder lens 39. If the laser beam directed toward the work piece 11 hits a coding strip 41, it is deflected in the direction of a convex lens 42 and focused onto a photodiode with an added amplifier device 43 lying in the focal range of the convex lens 42. The output signal of the photodiode with the amplifier device 43 is the path signal 17', which is also shown in FIG. 3.

The operation of the laser extensometer 33 is described as follows.

With a rotating mirror 36 driven by the motor 34 so it has a constant rotary motion, the laser beam, which is collimated by the cylinder lens 39 and deflected by the rotating mirror 36, sweeps the raster 40 attached to the work piece 11 in constant repetition, as is illustrated by the beam paths 44a–d, drawn in FIG. 4 and occurring in time sequence. If the laser beam 44 hits one of the raster's 40 reflecting coding strips 41, it is deflected and registered as a reflection of light by the photodiode with an amplifier device 43. As a consequence, the raster 40 is swept over once with each motor rotation, and a path signal 17', which produces an impulse each time the laser beam 44 is reflected on a coding strip 41, is produced at the outlet of the photodiode with the amplifier device 43.

Instead of the laser 37, a non-laser scanning source can, in principle, be provided, whereby in that case one must provide for a sufficient collimation of the scanning beam through an added collimator.

Figure 6:
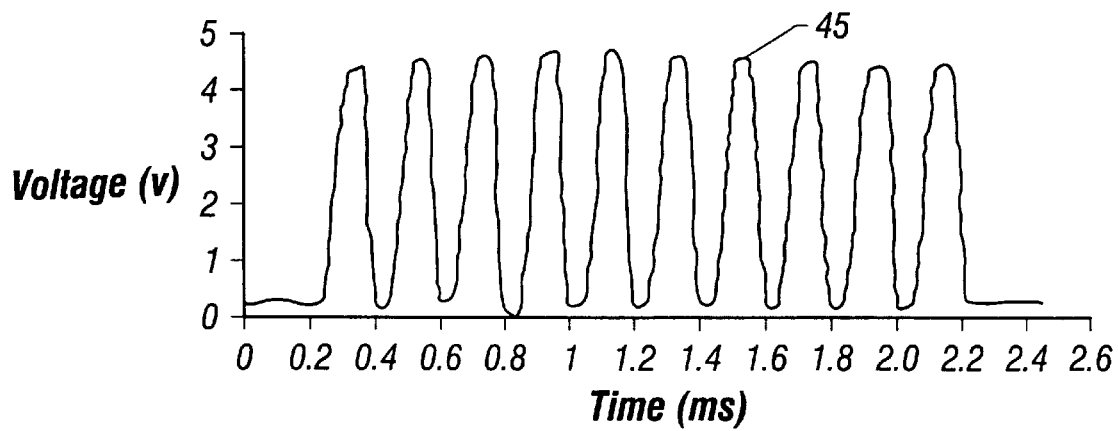
FIG. 6 shows a signal-stress time diagram of the output of the laser extensometer.
Figure 7:
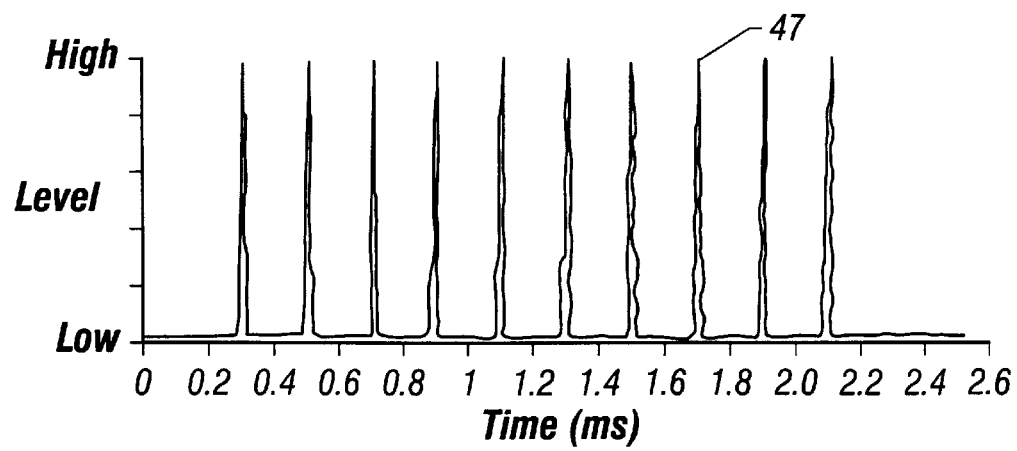
FIG. 7 shows a signal from FIG. 6 after a signal transformation.

FIG. 6 shows an impulse sequence obtained while the raster 40 is scanned, plotted as signal stress against time. Each of the ten impulses 45 originates from a reflection of the laser beam 44 on one of the ten coding strips 41 in FIG. 5. The impulse sequence shown in FIG. 6 is based on a scanning rate of 400 Hz (i.e., a rotating speed of the motor 34 of 400 UpS) and a coding strip width of a millimeter.

It is usually sufficient for the intensity modulation of the laser beam 44 if the coding strips have a diffuse scattering power that must only be distinguished from the scattering power of the raster areas lying between them. The coding strips 41 can, however, be designed as mirror reflection surfaces, and it is also plausible that with a transparent work piece a raster with different transmission properties is used and the transmitted laser beam is captured by the photodiode with an amplifier device 43.

The placement of the raster 40 (corresponds to the second direction) must not necessarily be coaxial to the direction that the power is introduced (first direction); when placing the raster 40 at a specified angle to the direction in which the power is introduced, measuring the mechanical-dynamic properties of the work piece at a slant to the direction in which the power is introduced is made possible.

According to FIG. 3, the path signal 17' is then transformed into a succession of discrete spikes, which occur at definite times and can, for example, be obtained in a transducer 46' within the framework of an analysis of the slope times of the impulse sequence represented in FIG. 6. The path signal 17' transformed in this way lies at the entrance of a multistop counter 48, which contains a counter driven by a high-frequency oscillator, whereby the counter is pushed into motion by an incoming spike and stopped by the next spike. The time information obtained between successive spikes is stored in a digital intermediate memory 49, to which a data processing unit 50 has access. In addition to the processor 50, the data processing unit 51 consists of the program memory 52, which is connected to the processor 50. The program memory 52 can, for instance, be made as a magnetic disk drive. In the memory 52 a process control program, computing program 52b, data processing program 52c, and graphics program, among other things, can be stored.

Moreover, the test stand according to the invention shown in FIG. 3 is distinguished from the known test stand according to FIG. 1 by the fact that controller 30' is provided instead of controller 30; controller 30' receives the power signal from the load cell 13 as well as another input signal from a path sensor 53, which is connected to the piston 7 of the servohydraulic testing machine 1, and sends a signal that corresponds to the path shift of the piston 7. Another servoloop, which makes possible a path-controlled dynamic stress of the work piece 11, is formed by the path sensor 53, the controller 30', and the pilot valve 5.

The control precision can be increased by the path control if one falls back on additional distance information which is not represented in the diagram and which is received from the path signal 17' and suitably processed in the processor 50.

The function generator 28' of the test stand according to the invention can essentially produce as many prespecified dynamic curves as desired, which then can be used as the basis according to the controller 30' both in the power- and path-controlled operation of the oscillation movements of the piston 7.

Below the operation of the test stand according to the invention will be described.

First, the desired test process is defined with the help of the process control program 52a by feeding in the routine parameters. The input parameters include, in particular, the following:

(a) the choice of the section of the work piece to be analyzed. For example, one can specify that a workpiece section is defined by each coding strip 41, as a result of which a maximal definition of the measurement is obtained. If only smaller definitions are necessary, then sections can be defined that are constructed from several coding strips. Similarly, it is possible for one to choose two particular sections selectively (e.g., the sections between the second and fourth and seventh and ninth coding strips 41) and that only these sections are analyzed with respect to their stress properties. By choosing suitable sections as a function of the form and type of the work piece analyzed, one can considerably reduce the data bank before performing the analysis;

(b) the choice of a suitable scanning frequency, by means of which the time definition of the analysis is defined. To guarantee the meaningful observation of an oscillation cycle, the scanning frequency must be larger than the oscillation frequency of the piston 7. Often the scanning frequency is at least 10 times larger than the oscillation frequency;

(c) the choice of the oscillation frequency;

(d) the choice of the form of oscillation, e.g., example, sine-shaped, triangular, or rectangular;

(e) the choice of the stress or length change area with a power- or path-controlled method of carrying out the test;

(f) in the case of stress-increase tests, especially the choice of the stress and timeframe of each stress level as well as the choice of the sequence of the stress levels chosen;

(g) in the case of repeated stress-increase tests, the choice of the number of repetitions of the stress-increase parameters specified in (f).

The process control program 52a can be designed, in addition, to monitor further process sequences. For instance, a source of heat or something similar can be addressed by the processor 50 through the process control program 52a.

The reference number 52b designates a computer program that serves to process the time information, stored in the intermediate memory 49, of the spike time differences determined by the multi-stop counter and to evaluate the hysteresis loop obtained for each chosen section of the work piece. During the measuring operation the computer program 52b calls up the corresponding time information stored in the intermediate memory 49 for each interesting workpiece section (defined beforehand by the process control program 52a) and calculates values for each section that designate the length changes of the corresponding section between two laser scans. The recalculation of the time data into length data, stored in the intermediate memory 49, takes place according to a calibration (carried out before the test starts) in which the measuring system learns the distance between the coding strips of the unextended or already stressed work piece as a reference length for the later measurement of the length extension via a self-calibrating process.

Figure 8:
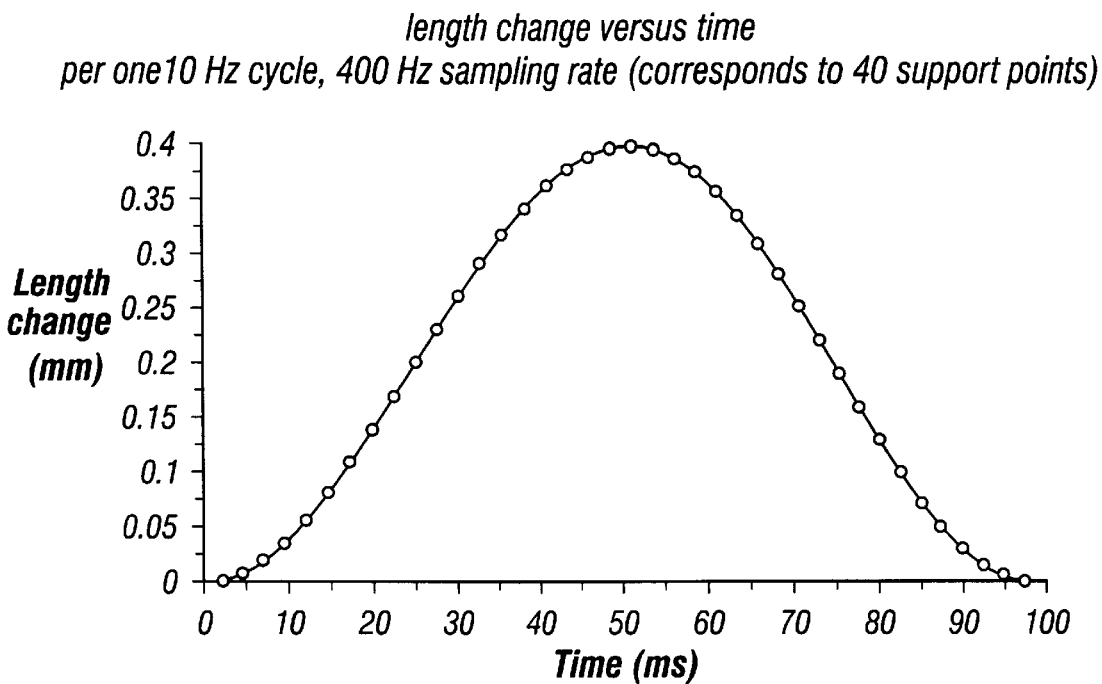
FIG. 8 shows a longitudinal change time diagram of a section of the analyzed work piece during one stress cycle.

FIG. 8 shows the length change of a single section during a 10-Hz stress cycle with a laser scanning rate of 400 Hz. The length change in the example under consideration ranges from 0 to 0.4 mm and is documented by 40 support positions that have accumulated through the 40 laser scans carried out during one stress cycle.

Figure 9:
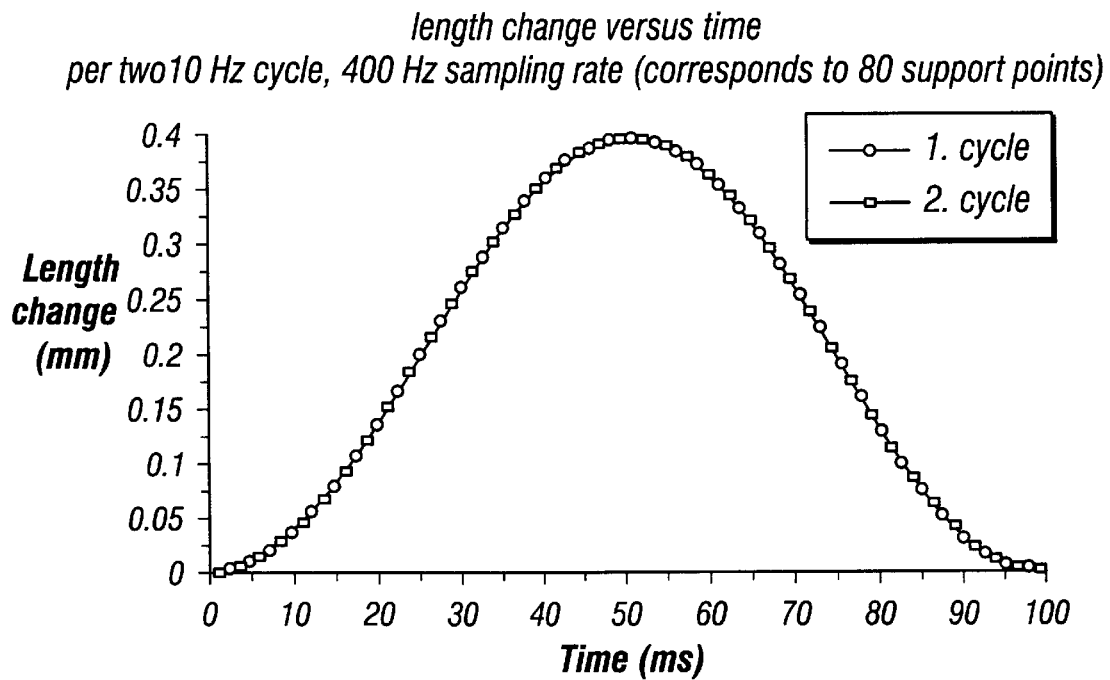
FIG. 9 shows a longitudinal change time diagram of the section from FIG. 8 during two stress cycles.

FIG. 9 also shows the length change of a special section of the work piece, plotted against time, whereby the data in this case have accumulated during two stress cycles, and thus the shape of the curve showing the length changes is based on the measurement of 80 support positions. In this connection circles designate the support positions obtained during the first cycle and squares designate those obtained during the second cycle.

Such an accumulation of the test points obtained during successive stress cycles is only meaningful if test points of different cycles do not coincide. This can be obtained by varying the scanning frequency by time ("wobbling") or by choosing the scanning frequency so it is asynchronous to the stress frequency.

Figure 10:
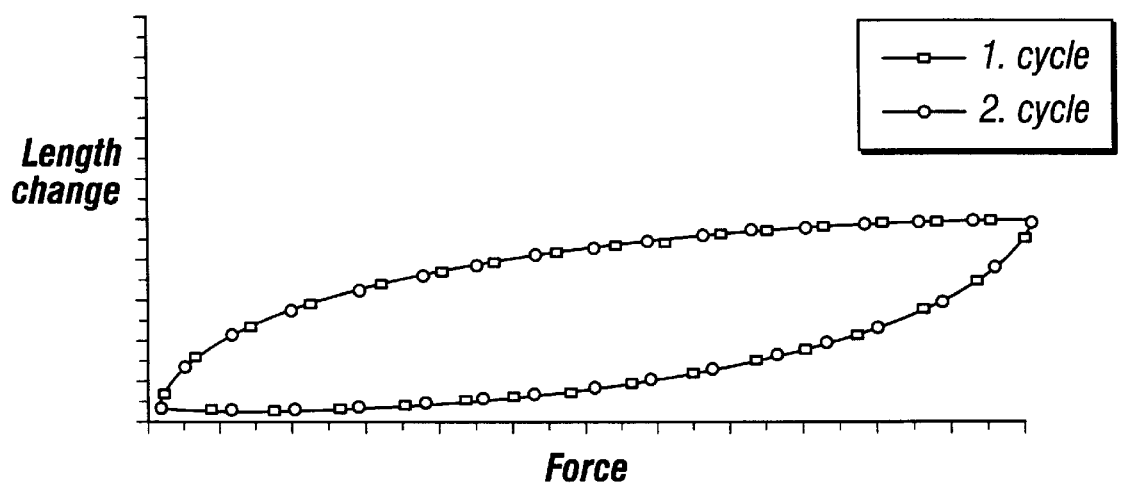
FIG. 10 shows a hysteresis loop of the section according to FIG. 9 plotted for two stress cycles.

FIG. 10 shows the hysteresis loop obtained for the workpiece section used as a basis for FIG. 9. In this case in FIG. 10 the length change determined according to FIGS. 8 and 9 is plotted on the y-axis and the power applied to the work piece each moment is plotted on the x-axis. The hysteresis loop in this case was constructed from the data obtained during two stress cycles (see FIG. 9), although it is nevertheless just as possible to construct the characteristic hysteresis loop for the deformation properties of the section during a single cycle (see FIG. 8) or to use data from three or more cycles. Although very quick changes of the stress properties can, in principle, be measured when using data from a few cycles to construct the hysteresis loop, the accumulation of data over several cycles offers the advantage of higher precision of the evaluation of the hysteresis loop obtained.

As an example, 100,000 oscillation cycles are carried out in an endurance test, whereby every five cycles are used to construct a local hysteresis loop. Between registering two hysteresis loops, 100 oscillation cycles occur in each case without registering data, whereby this number can be reduced if faster changes of the material properties are to be monitored.

The evaluation of the hysteresis loop shown in FIG. 10 is carried out in the known way (see FIGS. 2a, 2b, or 2c) by the computer program 52b, whereby one should nonetheless note that in contrast to the prior art, a hysteresis loop must now be evaluated for each of the chosen sections of the work piece, resulting in a higher computing output.

In addition to the accumulation of data, the interpolation-evaluation process, which is explained next, should preferably be used to obtain greater measuring precision. This process takes into consideration and corrects the problem that the coding strips 41 of the raster 40 are registered not at the same time, but with a certain time lag due to the finite scanning speed of the laser beam. As a result of the time lag, the values obtained for the extension display a phase shift compared to the values of the actual extension. This is undesirable, for the "fictitious" phase shift produced by the measurement enters into the phase shift $\phi$, which is determined by the hysteresis evaluation to characterize the material properties.

The interpolation-evaluation process is illustrated next with the use of FIGS. 11a to 15.

Figure 11A:
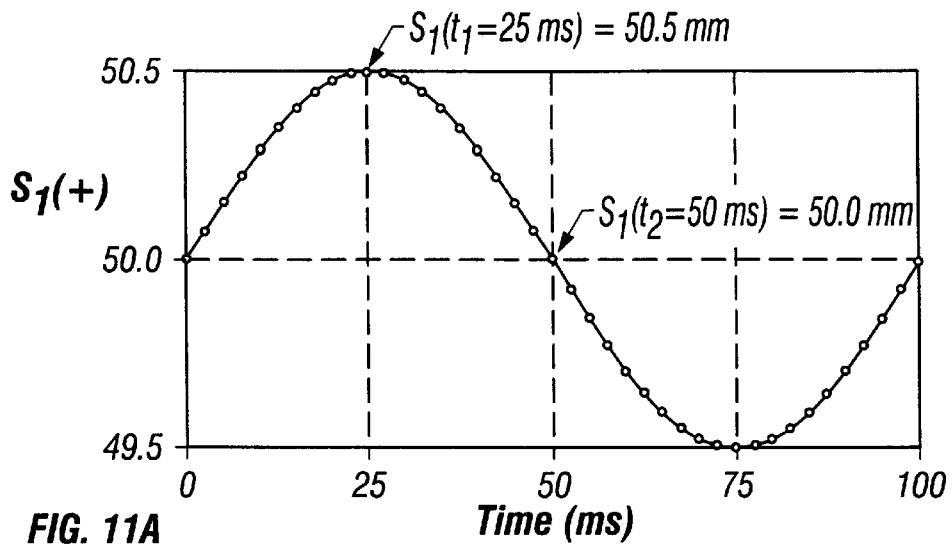
FIGS. 11a and 11b show coordinates of two coding strips $S_1$ and $S_6$ obtained at the respective scanning points during one stress cycle.

FIG. 11a shows the spatial coordinates of the oscillation of the first coding strip $S_1$ plotted against time. The diagram is based on a scanning rate of 400 Hz with a stress frequency of 10 Hz. The 40 support positions provided during one stress cycle have a time interval of 2.5 ms.

Figure 11B:
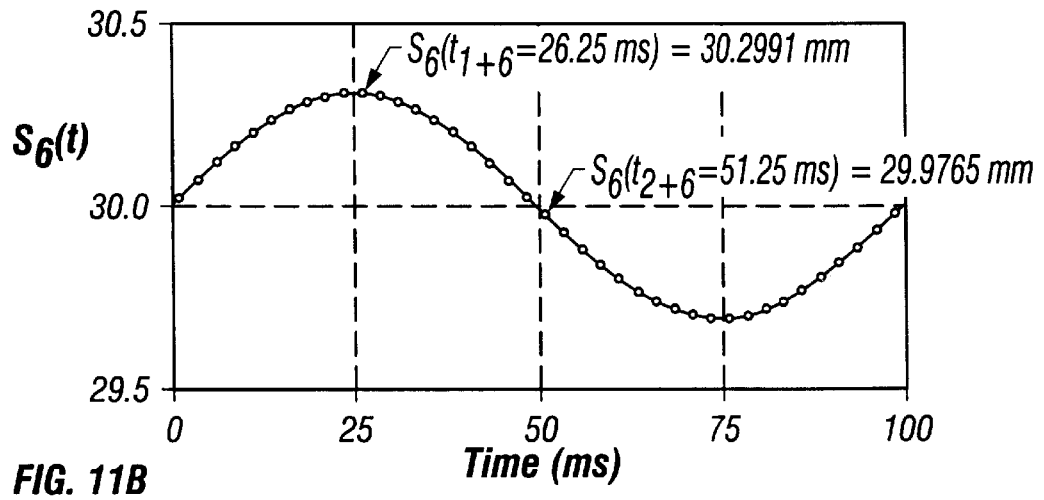

FIG. 11b shows the same information as in FIG. 11a for another coding strip $S_6$, which lies 20 mm from the first coding strip $S_1$ shown in FIG. 11a. Each of the support positions has shifted 1.25 ms compared to the diagram in FIG. 11a because the light spot requires the time to sweep the stretch between the two strips $S_1$ and $S_6$.

Figure 11C:
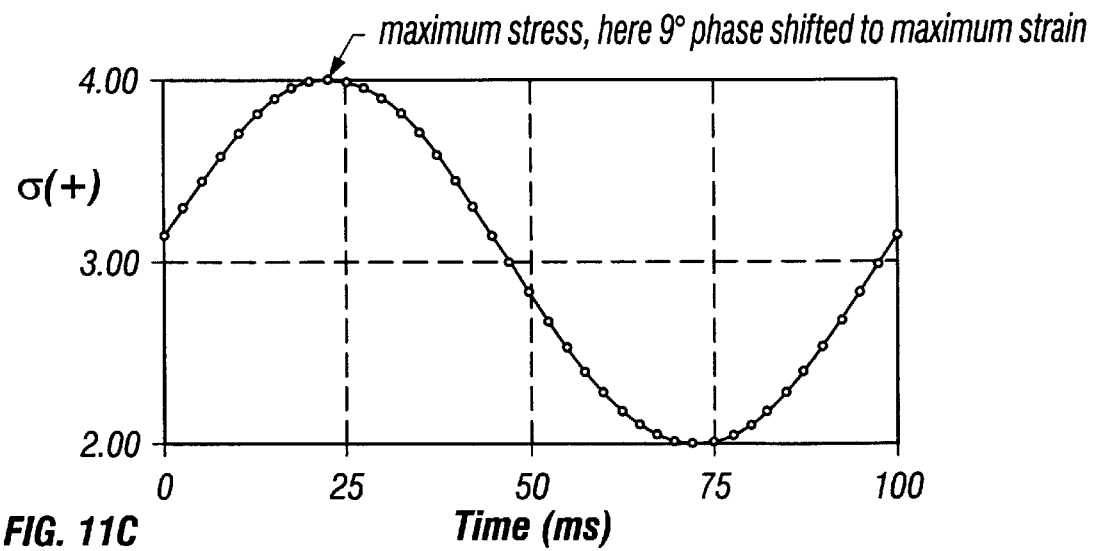
FIG. 11c shows a stress time diagram for the section between the coding strips $S_1$ and $S_6$ during one stress cycle.
Figure 12:
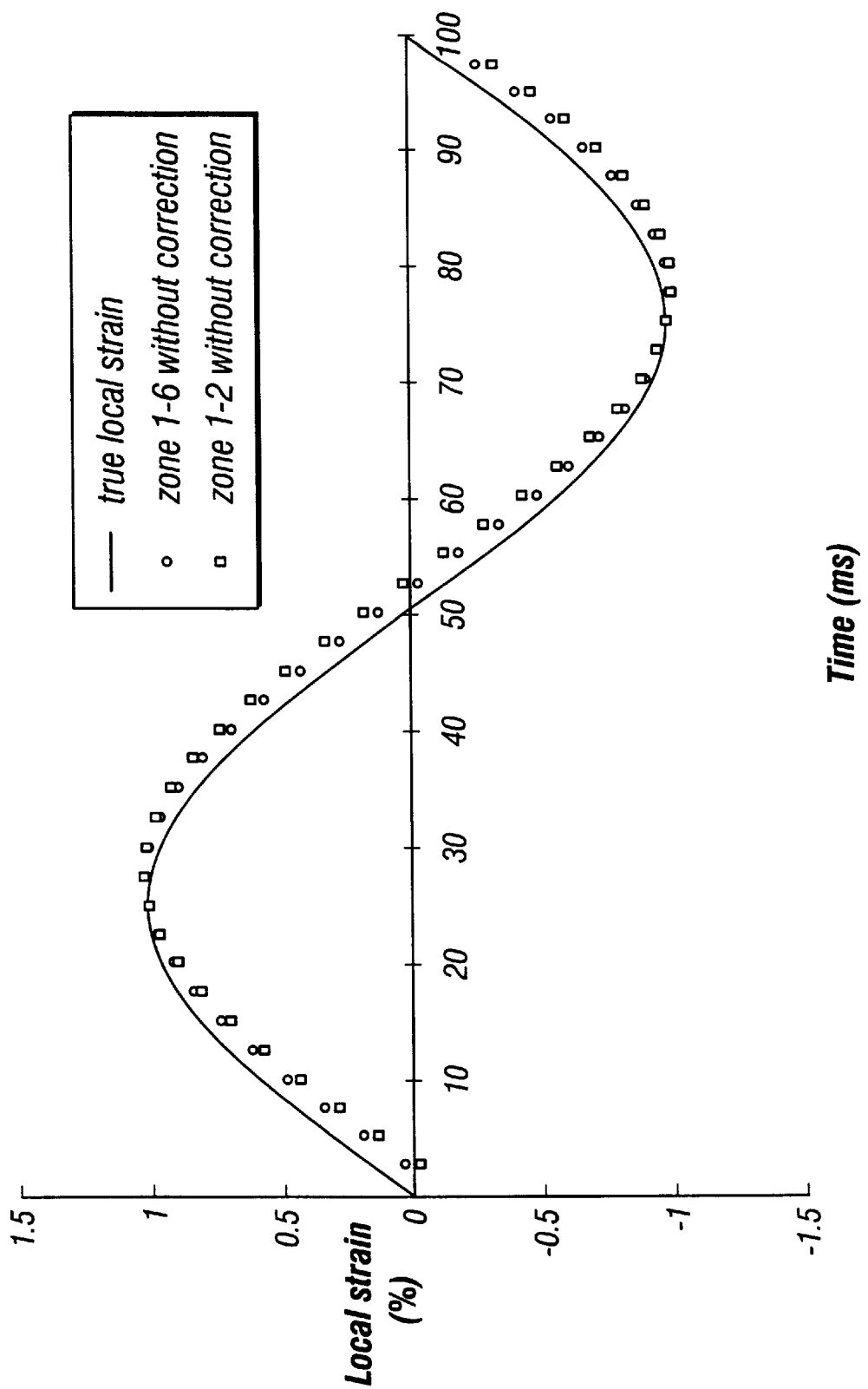
FIG. 12 shows a longitudinal change time diagram for the sections between the coding strips $S_1$ and $S_2$ or $S_1$ and $S_6$ during one stress cycle without correction of the recorded values.

FIG. 11c shows the time path of the stress measured $\sigma(t)$. It displays a phase shift to the oscillation curves shown in FIGS. 11a and 11b, which is caused by material effects. In the example shown, the phase shift is 9°. The values for the stress $\sigma(t)$ are plotted at the same time as the spatial coordinates of the first coding strip $S_1$, i.e., on the support positions of FIG. 11a.

On these support positions there are, however, no spatial coordinates for the coding strip $S_1$. This means that the values obtained for the length change of the section between the two coding strips $S_1$ and $S_6$ do not exactly correspond to the actual length change.

This is illustrated by using an example. Given t=50 ms (a half-cycle) and homogenous workpiece properties, the actual relative length change must be equal to 0 everywhere (and thus also between the strips $S_1$ and $S_6$). Because, however, at each time point t=50 for the second coding strip $S_6$ no support position exists and thus also no spatial coordinates exist, the result is a relative length change that is not equal to 0:

$$[S_1(t = 50 \text{ ms}) - S_1(t = 0 \text{ ms})] -$$
$$[S_6(t = 51.25 \text{ ms}) - S_6(t = 0 \text{ ms}) = [0] - [29.9765 - 30] = 0.0235 \text{ mm}.$$

The consequence for this "fictitious" length change is that both the phase and amplitude of the calculated relative extension deviate from the curve of the actual relative extension. This state of affairs is represented graphically in FIG. 12. The continuous curve represents the true local extension (in %), while the values designated by a diamond ◇ give the (uncorrected) extension properties between the strips $S_1$ and $S_6$ (20-mm distance); and the extension values designated by a square ☐, the corrected) extension properties between the first coding strip $S_1$ and the coding strip $S_2$ (4-mm distance) directly adjacent to it. Both curves of the test values clearly deviate from the true extension.

The evaluation process according to the invention is now essentially based on the fact that the "missing" support positions in FIG. 11b are added (those are the support positions used in FIGS. 11a and 11c, e.g., $t_i$=25 ms) and the respective values of the spatial coordinates of $S_6$ are obtained through an interpolation of the curve.

Figure 13A:
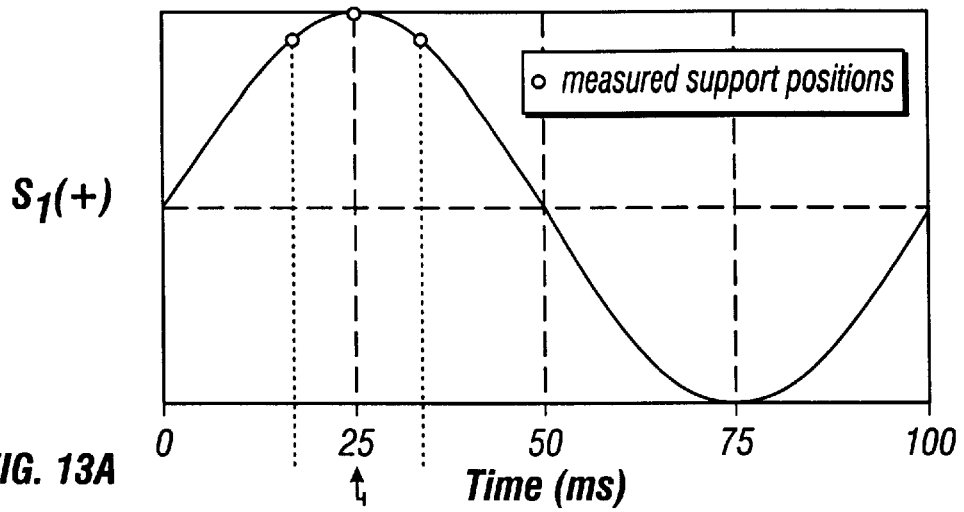
FIGS. 13a, b, and c show representations corresponding to FIGS. 11a, b, and c.
Figure 13B:
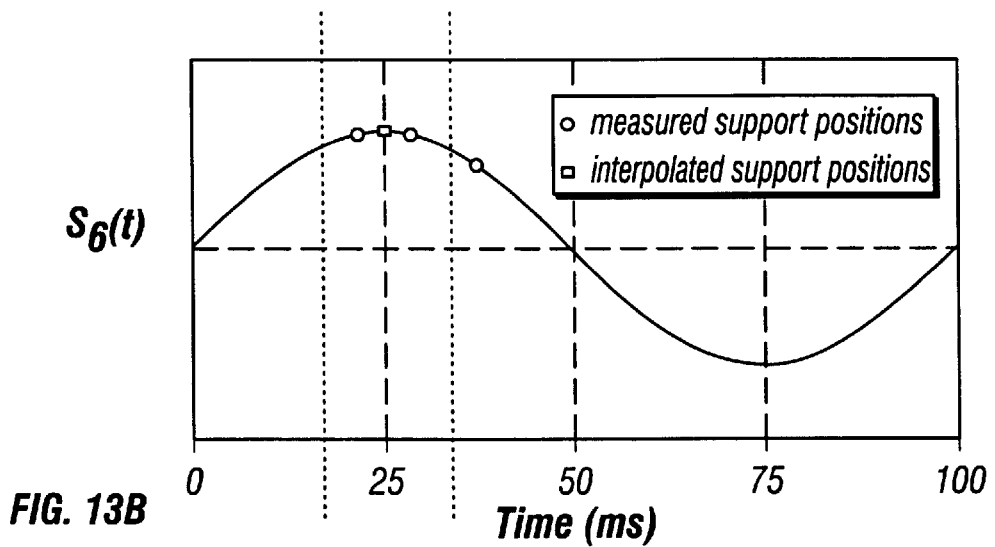
Figure 13C:
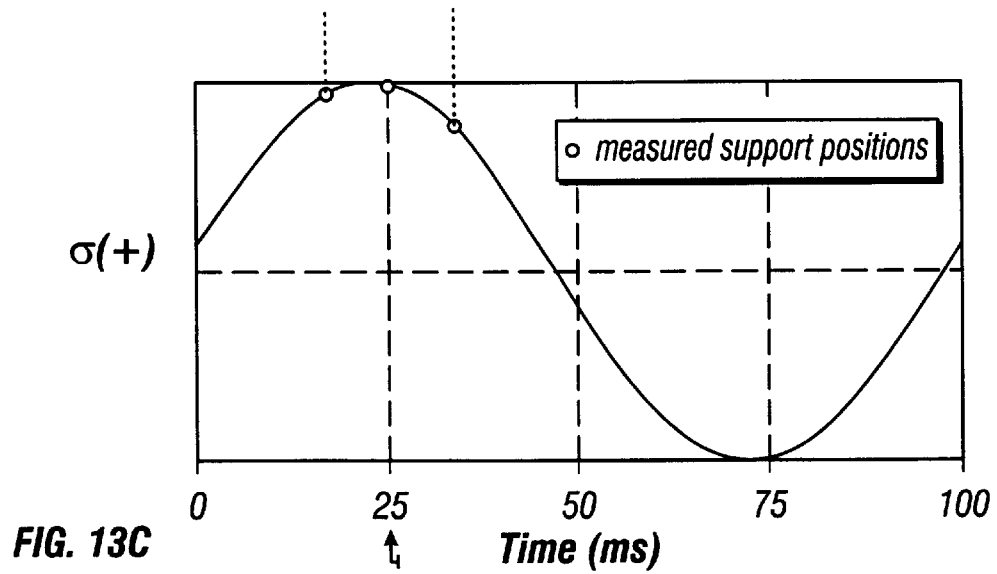

The interpolation step is explained in FIGS. 13a–c. FIGS. 13a–c correspond to FIGS. 11a–c, although larger distances between the support positions have been drawn in to make grasping the relationships easier and quicker. It is clear that additional support positions ☐ are generated at the discrete time points $t_i$ and the respective values of the function $S_6(t_i)$ are determined by interpolation at the additional support positions ☐ and used as output values for additional calculations.

A polynomial of the first or a higher order can be used for interpolation.

Figure 14:
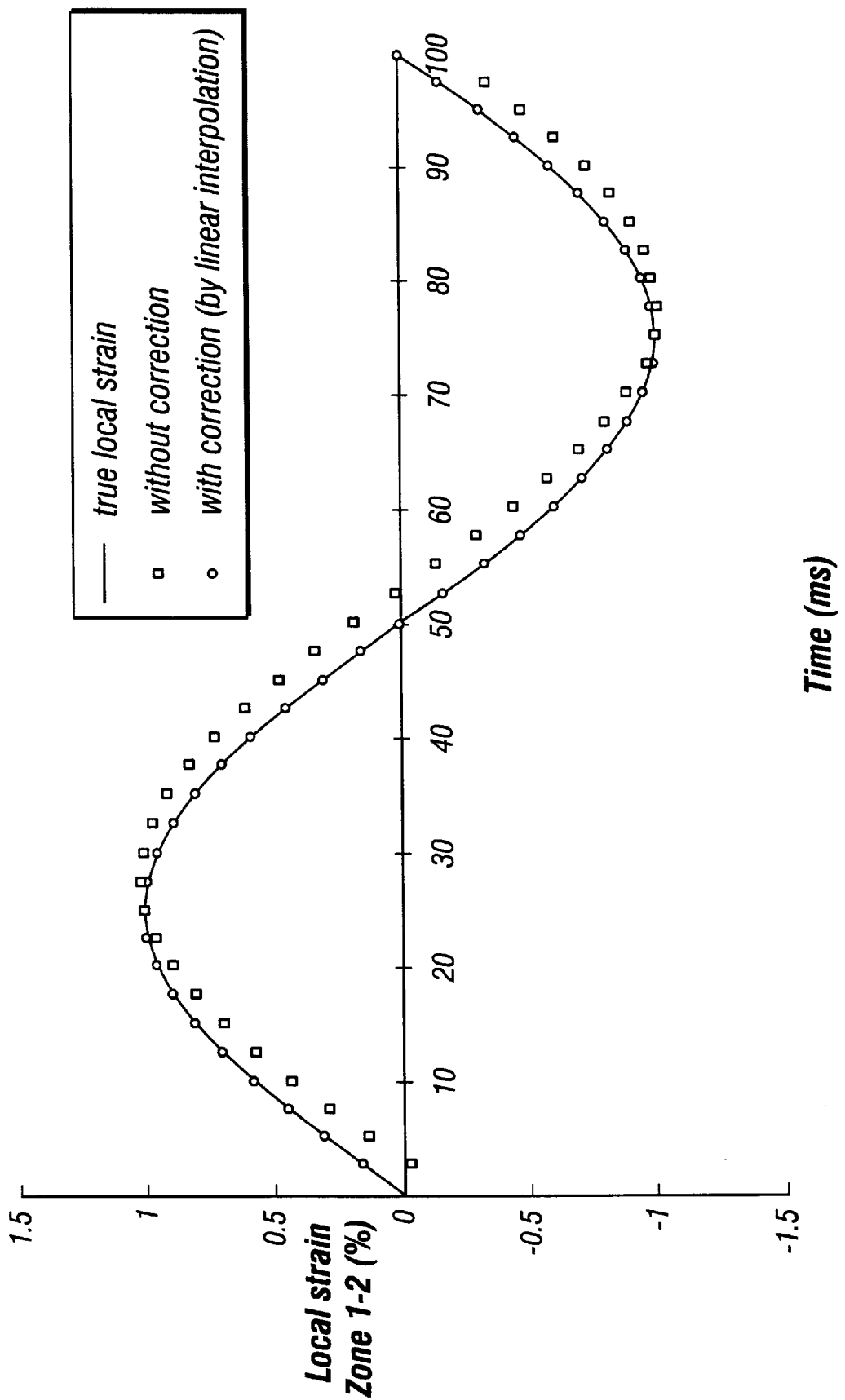
FIG. 14 shows a longitudinal-change time diagram of the section between the coding strips $S_1$ and $S_2$ during one stress cycle with and without correction of the recorded values.
Figure 15:
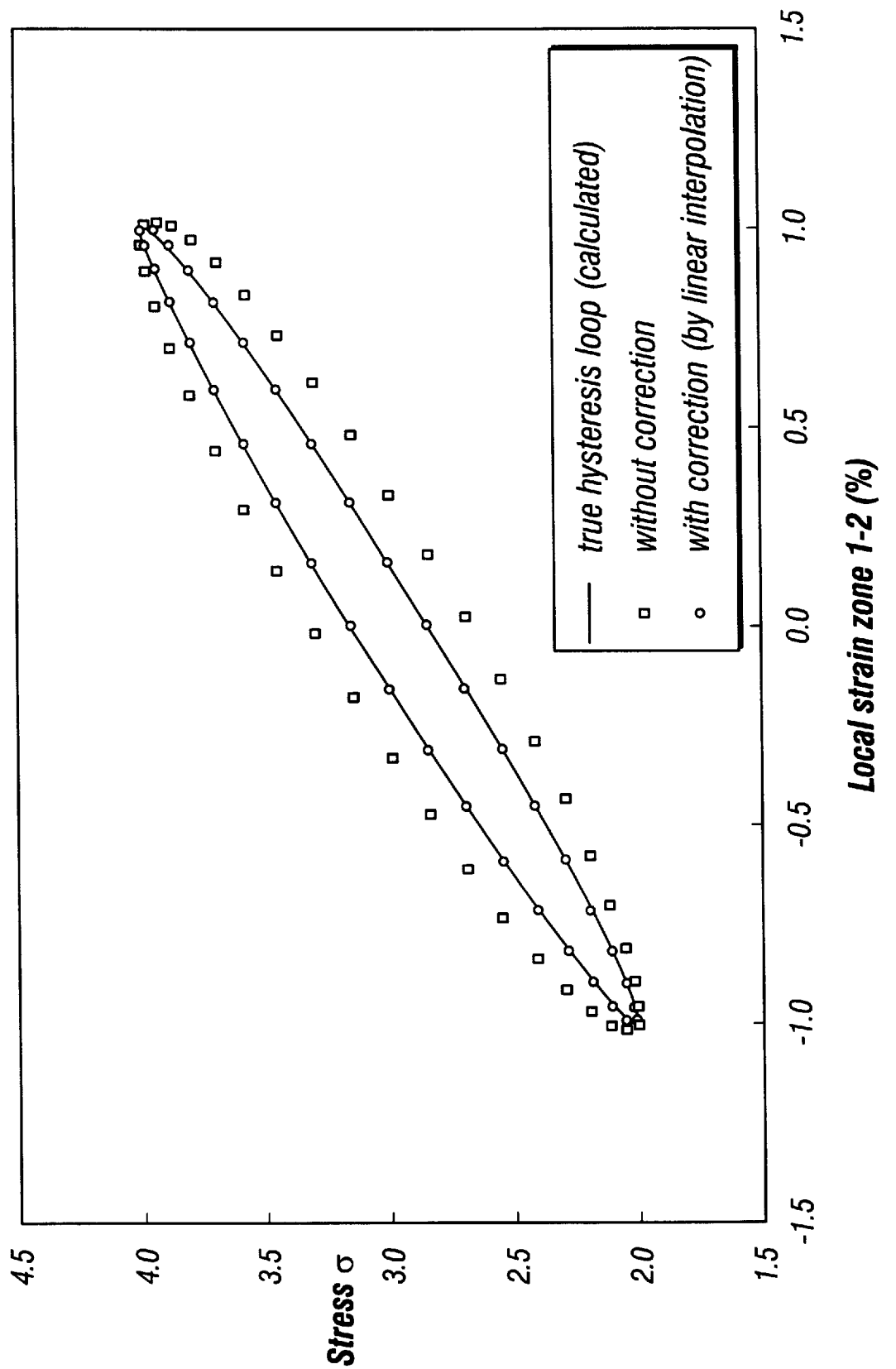
FIG. 15 shows a hysteresis loop of the section between the coding strips $S_1$ and $S_2$ during one stress cycle with and without correction of the plotted values.

In FIGS. 14 and 15 the values obtained for the extension (FIG. 14) and the hysteresis loop (FIG. 15) are drawn in, as well as the values obtained without correction ☐ and those obtained with correction ○. In both cases it is shown that linear interpolation leads to a clear improvement of the test results.

The values for the internal damping $\Lambda$, the material stiffness tan $\alpha_1$, tan $\alpha_2$ of the mean extension $\epsilon_{mean}$ of the plastic extension $\epsilon_p$, or the loss can be determined as characteristic values. Due to corrections made, these values now exclusively characterize the material properties.

The further processing of the characteristic values obtained is carried out with the help of the data processing program 52c. The data processing can include, in particular, the following functions, depending on one's need:

(a) the comparison of the values of a certain characteristic value obtained for different sections and the derivation of the distribution of the values for the section with respect to position. In this way statements can be made with respect to locally different material properties under dynamic stress;

(b) the comparison of the time paths of the values obtained for the different sections. In this way locally different speeds of workpiece deterioration can be recognized;

(c) within the framework of repeated stress-increase tests the comparison of section values of a characteristic value obtained during a first. stress-increase sequence with the corresponding values (i.e., at the same stress level) obtained for a subsequent stress-increase sequence. This comparison provides information about the stress limits above which irreversible damaging processes can occur with changes in stress.

In addition, within the framework of the data processing program the processing of additional test values fed to the processor 50, as, for instance, cross-dimension test values (see also FIG. 16) or temperature test values, can be provided.

Finally, as an option a graphics program 52d can be provided that constantly transforms the values obtained by the computer program 52b for the characteristic values or the comparative values determined by the data processing program 52c in such a way that they can be made visible on a monitor as a graphical representation, for example, by using a false-color representation of the work piece. Because the total evaluation control including the multi-stop counter 48, the intermediate memory 49, and the data processing unit 51 can be operated with a suitable design, the graphics program 52d enables one to follow every desired characteristic value with respect to its distribution over the work piece and its development over time during the course of the test. As a result, data about the stress properties can be obtained in a single test—especially for nonhomogeneous or multi-component work pieces—that either could not be obtained up to now or could only be obtained at a great expense by carrying out many successive measurements on as many identical work pieces (which in practice are never truly identical) as possible.

In summary, one can go out from the assumption that the invention will make possible a considerable advance in the area of the assessment of the stress and fatigue properties of different work pieces.

Figure 16:
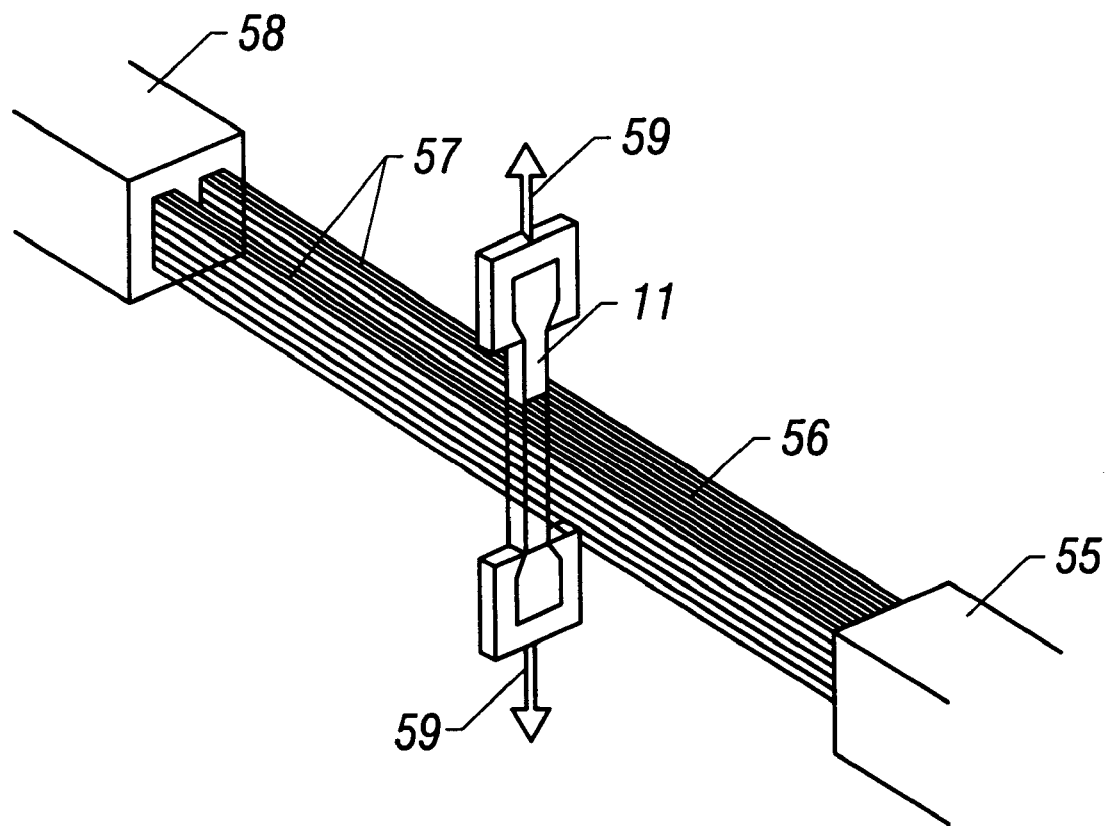
FIG. 16 shows a working example of a device used in the procedure according to the invention to determine the ratio of the workpiece's longitudinal extension to its contraction in width (Poisson's ratio).

FIG. 16 serves to illustrate another different variation of the procedure according to the invention that was already mentioned and that makes possible a measurement of the cross dimension of the work piece 11 and thus a calculation of its Poisson's ratio. In this connection the work piece 11 is exposed to rays from a stationary pencil of light 56 that are emitted by a light source 55 and whose width is larger than the cross dimension of the work piece 11 so that the work piece 11 shades only a part of the pencil of light 56 and two residual pencils of light 57 on both sides of the work piece go past them. The residual pencils of light fall on a detector 58, which emits a signal that reproduces the intensity of the residual pencil of light 57 received and is thus a measure for the momentary width of the work piece 11. If the work piece 11 is extended according to the arrows 59 within the framework of a tensile stress, its width is reduced so that the shading decreases and the intensity of the residual pencil of light 57 increases. Correspondingly, compression stress of the work piece 11 causes an expansion of the work piece and thus a decrease of the residual pencil of light registered by the detector 58. The height of the pencil of light 56 can be varied according to the desired definition. The detector's 58 output signal can, if applicable, be fed—after the processor 50 is reinforced and digitized (in a way not depicted in the diagrams)—and considered in the signal evaluation.

Although during the measuring procedure illustrated in FIG. 16 only one change of the total width of the work piece can be observed, the change in the width distribution over the width of the work piece can be measured according to another variation in the model. To do so it is necessary to provide the work piece 11 with another raster made of contrasting coding strips, whereby the coding strips now run in longitudinal direction in contrast to the raster represented in FIG. 5. The measurement of the change in the width distribution of the work piece 11 then follows analogously to the determination already described in connection with FIG. 4, whereby the laser beam scanning the other raster must now be guided over the work piece in the transverse direction instead of in the longitudinal direction, deviating from FIG. 4. Signal processing and the evaluation of the cross dimension signal (analogous to the path signal 17') obtained in this way takes place in essentially the same way as that already described in connection with the measure of the length extension.

The simultaneous measure of the distribution of the cross dimension and length extension on the same work piece 11 during a test makes possible the analysis of the local material properties in two dimensions and therefore supplies additional information with respect to local phenomena, for instance, the formation of cracks in the work piece and the like. In a way that is not represented in the diagrams, one can, furthermore, have the work piece warmed or cooled locally or over the entire workpiece section analyzed while carrying out the test, whereby the warming and cooling processes are preferably carried out without contact with the object, and in the case of warming, it occurs, for example, inductively or through a warming pencil of light emitted by a warming light source. Such tests can provide information about the functional relationship between workpiece fatigue and temperature under dynamic stress.

A device for carrying out the procedure according to the invention is not limited to the working models described in connection with FIGS. 1 to 16. For example, the servohydraulic testing machine 1 can be replaced by an electrically driven pulsator with a corresponding control circuit. Moreover, the use of a multi-stop counter 48 and intermediate memory 49 to process the (if applicable) transformed path signal 17' is not necessarily required because obtaining the corresponding data for the section length change can only be carried out by the processor 50—even within a framework of a fast Fourier analysis (FFA) of the path signal 17'.

What is claimed is:

1. A method for investigating the mechanical dynamic properties of a work piece, the method comprising:

subjecting the work piece to at least one of cyclical tensile and cyclical compression stress along a first direction, producing a power signal representing the at least one of the tensile and compression stress of the work piece using a power-registering device, producing a distance signal representing a length change of at least one specified section of the work piece using a distance-registering device, and feeding the power signal and the distance signal to an evaluation device that determines, from the power signal and distance signal obtained during at least one stress cycle, at least one of the characteristic values ($\Lambda$; tan $\alpha_1$; tan $\alpha_2$; $\epsilon_{mean}$; $\epsilon_p$) with respect to the work pieces damping properties or at least one of tensile and compression stiffness properties, nonelastic deformation properties, and plastic extension properties for the mechanical-dynamic properties of the specified section of the work piece, wherein the work piece is provided with a raster made of contrasting coding strips along a second direction and is swept by a laser beam with a prespecified scanning frequency running along a second direction within the framework of registering the distance, whereby the scanning frequency of the laser beam is larger than the frequency with which the work piece undergoes the at least one of cyclical tensile and cyclical compression stress, the intensity of the laser light modulated by the coding strips of the raster is registered and its time path forms the distance signal, and whereby the evaluation device registers the length changes of different sections of the work piece, swept over by the laser light and defined in each case by two or more neighboring coding strips, from the time path of the distance signal and determines the characteristic value(s) for the mechanical-dynamic properties ($\Lambda$; tan $\alpha_1$; tan $\alpha_2$; $\epsilon_{mean}$; $\epsilon_p$) of the different sections of the work piece.

2. The method of claim 1, wherein the first direction coincides with the second direction.

3. The method of claim 1, wherein the scanning frequency of the laser beam is at least 10 times larger than the frequency with which the work piece is subjected to the at least one of cyclical tensile or cyclical compression stress.

4. The method of claim 1, wherein when calculating the length changes of different sections, the evaluation device assigns a certain absolute reference time ($t_i$) to each laser scan and for each laser scan the determination of the length changes of the different sections occurs with respect to each assigned reference time ($t_i$).

5. The method of claim 1, wherein the power signal is digitized by using an A/D converter, and a digital section length-change signal, which represents the length change of the corresponding section between two successive laser scans, is obtained from the distance signal (if applicable, previously transformed by an impulse), for each section of the work piece and the characteristic value(s) ($\Lambda$; tan $\alpha_1$; tan $\alpha_2$; $\epsilon_{mean}$; $\epsilon_p$) is/are determined for one or more stress cycles and for each section of the work piece from the digital power signal and the digital section length-change signals by means of a computer program stored in a data processing unit.

6. The method of claim 1, wherein at least one of the damping distribution curve, tensile curve, compression stiffness curve, and the non-elastic deformation distribution curve is determined over the entire workpiece section swept by the laser beam.

7. The method of claim 1, wherein the cyclical stress is carried out in the tensile, compression, or alternating tensile-compression area.

8. The method of claim 1, wherein the work piece partially shades a stationary pencil of light emitted from a light source with a cross dimension that is larger than the cross dimension of the work piece and that the intensity of the residual light not shaded by the work piece is transformed into a signal characterizing the cross dimension of the work piece.

9. The method of claim 8, wherein the extension of the light spot in the second direction produced by the pencil of light on the work piece essentially corresponds to the length of one or several observed sections of the work piece.

10. The method of claim 1, wherein the work piece is provided with another raster made of contrasting coding strips in a third direction; the work piece is swept by another laser beam with another scanning frequency along the third direction, whereby the additional scanning frequency of the additional laser beam is larger—in particular, 10 times larger than the frequency with which the work piece is subjected to the at least one of cyclical tensile and cyclical compression stress;

and the intensity of the additional laser beam modulated by the coding strip of the other raster is registered and its time path forms another distance signal, which is fed to the evaluation device and from whose time path the evaluation device determines the extension distribution of the work piece along the third direction locally in the area of the additional raster.

11. The method of claim 10, wherein the third direction runs vertical to the first direction in such a way that the additional distance signal for the distribution of the cross dimension of the work piece is characteristic.

12. The method of claim 8, wherein the cross dimension or the signal characterizing the distribution of the cross dimension of the work piece is compared to the signal characterizing the length change of one or several sections of the work piece, if applicable, after calibration.

13. Device for investigating the mechanical-dynamic properties of a work piece, comprising a pulsator which subjects the work piece to at least one of a cyclical tensile and a cyclical compression stress along a first direction, a power-registering device, which produces a power signal representing the at least one of the cyclical tensile or cyclical compression stress of the work piece, a distance-registering device which produces a distance signal representing a length change of at least one specified section of the work piece, and an evaluation device to which is fed the power signal and distance signal and which determines at least one of the characteristic values ($\Lambda$; tan $\alpha_1$; tan $\alpha_2$; $\epsilon_{mean}$; $\epsilon_p$) for the mechanical-dynamic properties of the specified section of the work piece with respect to at least one of its damping properties, tensile properties, compression properties, nonelastic deformation properties, and plastic extension properties from the power signal and distance signal obtained during one or several stress cycles, wherein the distance-registering device contains a laser having a laser beam that constantly sweeps the work piece, which is provided with a raster along a second direction that is made of contrasting coding strips, with a prespecified scanning frequency running along the second direction, whereby the scanning frequency of the laser beam is larger than the frequency with which the work piece is subjected to the at least one of cyclical tensile or cyclical compression stress, the distance-registering device also includes a photodetector device which registers the intensity of the laser light modulated by the coding strips of the raster and gives its time path as a distance signal; and the evaluation device registers from the time path of the distance signal the length changes of different sections of the workpiece section swept by the laser light and defined by two or more neighboring coding strips and determines the characteristic values for the mechanical-dynamic properties ($\Lambda$; $\tan \alpha_1$; $\tan \alpha_2$; $\epsilon_{mean}$; $\epsilon_p$) for the different sections of the work piece.

14. Device according to claim 13, wherein the sections of the work piece are defined by two successive coding strips of the raster.

15. Device according to claim 13, wherein the center distance of two successive coding strips lies in the range of 0.5 to 10 mm, and especially between 2 and 5 mm.

16. Device according to claim 13, further comprising a heating or cooling device which warms or cools the work piece locally and temporarily, if applicable.

17. Device according to claim 16, wherein the heating or cooling device makes possible warming or cooling the work piece without contact to the object and in the case of a heating device is done, in particular, by at least one of induction heating, an air-circulating oven, and a warming light source directed onto the work piece.

* * * * *